United States Patent
O'Reilly et al.

(10) Patent No.: US 7,054,755 B2
(45) Date of Patent: May 30, 2006

(54) INTERACTIVE CORRELATION OF COMPOUND INFORMATION AND GENOMIC INFORMATION

(75) Inventors: David J. O'Reilly, Mountain View, CA (US); Alan H. Roter, Mountain View, CA (US); Keith Bostian, Mountain View, CA (US); David J. Morgans, Jr., Los Altos, CA (US)

(73) Assignee: Iconix Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/977,064

(22) Filed: Oct. 11, 2001

(65) Prior Publication Data

US 2002/0174096 A1    Nov. 21, 2002

Related U.S. Application Data

(60) Provisional application No. 60/240,118, filed on Oct. 12, 2000.

(51) Int. Cl.
  *G01N 33/48*    (2006.01)
  *C12Q 1/68*    (2006.01)
  *G06F 7/00*    (2006.01)

(52) U.S. Cl. .................... 702/19; 702/20; 707/102; 703/11; 435/6

(58) Field of Classification Search ............ 702/19–20; 703/11; 435/6; 707/102
  See application file for complete search history.

(56) References Cited

U.S. PATENT DOCUMENTS 5,930,154 A    7/1999    Thalhammer-Reyero 6,291,182 B1    9/2001    Schork et al.
6,453,241 B1 *    9/2002    Bassett et al. ................ 702/19
2002/0032530 A1 *    3/2002    Pati et al. .................... 702/20

FOREIGN PATENT DOCUMENTS

| EP | 0935210 A2 | 8/1999 |
|---|---|---|
| EP | 01891547 | 10/2001 |
| WO | WO 96/23078 | 8/1996 |
| WO | WO 99/58720 | 5/1999 |
| WO | WO 00/50889 | 2/2000 |
| WO | WO 00/50889 | 8/2000 |
| WO | WO 00/65421 | 11/2000 |

OTHER PUBLICATIONS

Sorace et al., "Functional Bioinformatics: The Cellular Response Database", Frontiers in bioscience, vol. 2, Nov. 1, 1997.

Weinstein et al., "An Information-Intensive Approach to the Molecular Pharmacology of Cancer", Science, vol. 275, Jan. 17, 1997, pp. 343-349.

Weinstein, J.N., et al., "An Information-Intensive Approach to the Molecular Pharmacology of Cancer" Science 275:343-349 (1997).

Sorace, J., et al. "Functional Bioinformatics: the Cellular Response Database" Frontiers In Bioscience 2:33-36, (1997).

* cited by examiner

*Primary Examiner*—Mary K. Zeman
(74) *Attorney, Agent, or Firm*—Howrey LLP; Adam K. Whiting

(57) ABSTRACT

An interactive system for facilitating hypothesis construction by correlating and presenting gene expression data, bioassay data, and compound activity data, and associating gene and compound function information with product information, and facilitating product purchase, is disclosed.

14 Claims, 2 Drawing Sheets

INTERACTIVE CORRELATION OF COMPOUND INFORMATION AND GENOMIC INFORMATION

CROSS-REFERENCE TO RELATED APPLICATION

This application is related to provisional patent application Ser. No. 60/240,118 filed Oct. 12, 2000, from which priority is claimed under 35 USC §119(e)(1) and which is incorporated herein by reference in its entirety.

FIELD OF THE INVENTION

This invention relates to methods and products for identifying pharmaceutical leads, correlating information regarding gene expression, biological assays and other relevant information, and facilitating the purchase of related products.

BACKGROUND OF THE INVENTION

Genomic sequence information is now available for several organisms, and additional data is added continuously. However, only a small fraction of the open reading frames now sequenced correspond to genes of known function: the function of most polynucleotide sequences, and any encoded proteins, is still unknown. These genes are now studied by means of, inter alia, polynucleotide arrays, which quantify the amount of mRNA produced by a test cell (or organism) under specific conditions. "Chemical genomic annotation" is the process of determining the transcriptional and bioassay response of one or more genes to exposure to a particular chemical, and defining and interpreting such genes in terms of the classes of chemicals for which they interact. A comprehensive library of chemical genomic annotations would enable one to design and optimize new pharmaceutical lead compounds based on the probable transcriptional and biomolecular profile of a hypothetical compound with certain characteristics. Additionally, one can use chemical genomic annotations to determine relationships between genes (for example, as members of a signal pathway or protein-protein interaction pair), and aid in determining the causes of side effects and the like. Finally, presenting the drug design researcher with a body of chemical genomic annotation information will generate research hypotheses that will stimulate follow-on experimental design, and therefor enable and stimulate purchase of related products to execute such experiments.

Sabatini et al., U.S. Pat. No. 5,966,712 disclosed a database and system for storing, comparing and analyzing genomic data.

Maslyn et al., U.S. Pat. No. 5,953,727 disclosed a relational database for storing genomic data.

Kohler et al., U.S. Pat. No. 5,523,208 disclosed a database and method for comparing polynucleotide sequences and the predicted functions of their encoded proteins.

Fujiyama et al., U.S. Pat. No. 5,706,498 disclosed database and retrieval system, for identifying genes of similar sequence.

SUMMARY OF THE INVENTION

We have now invented a system and method for analyzing and exploring the data resulting from chemical genomic annotation experiments, and for facilitating the design by a user of further experiments related to the user's goals, and thereby encouraging the purchase by the user of products related to the data and additional experiments.

One aspect of the invention is a method for evaluating a test compound for biological activity, comprising: providing a database comprising a plurality of reference gene expression profiles, each profile comprising a representation of the expression level of a plurality of genes in a test cell exposed to a reference compound and a representation of the reference compound; providing a test gene expression profile, comprising a representation of the expression level of a plurality of genes in a test cell exposed to said test compound; comparing said test gene expression profile with said first gene expression profiles; identifying at least one first gene expression profile that is similar to said test gene expression profile; displaying said selected expression profile, and displaying product information related to said selected expression profile.

Another aspect of the invention is a system for performing the method of the invention.

Another aspect of the invention is a computer-readable medium having encoded thereon a set of instructions enabling a computer system to perform the method of the invention.

DETAILED DESCRIPTION

Definitions

Figure 1:
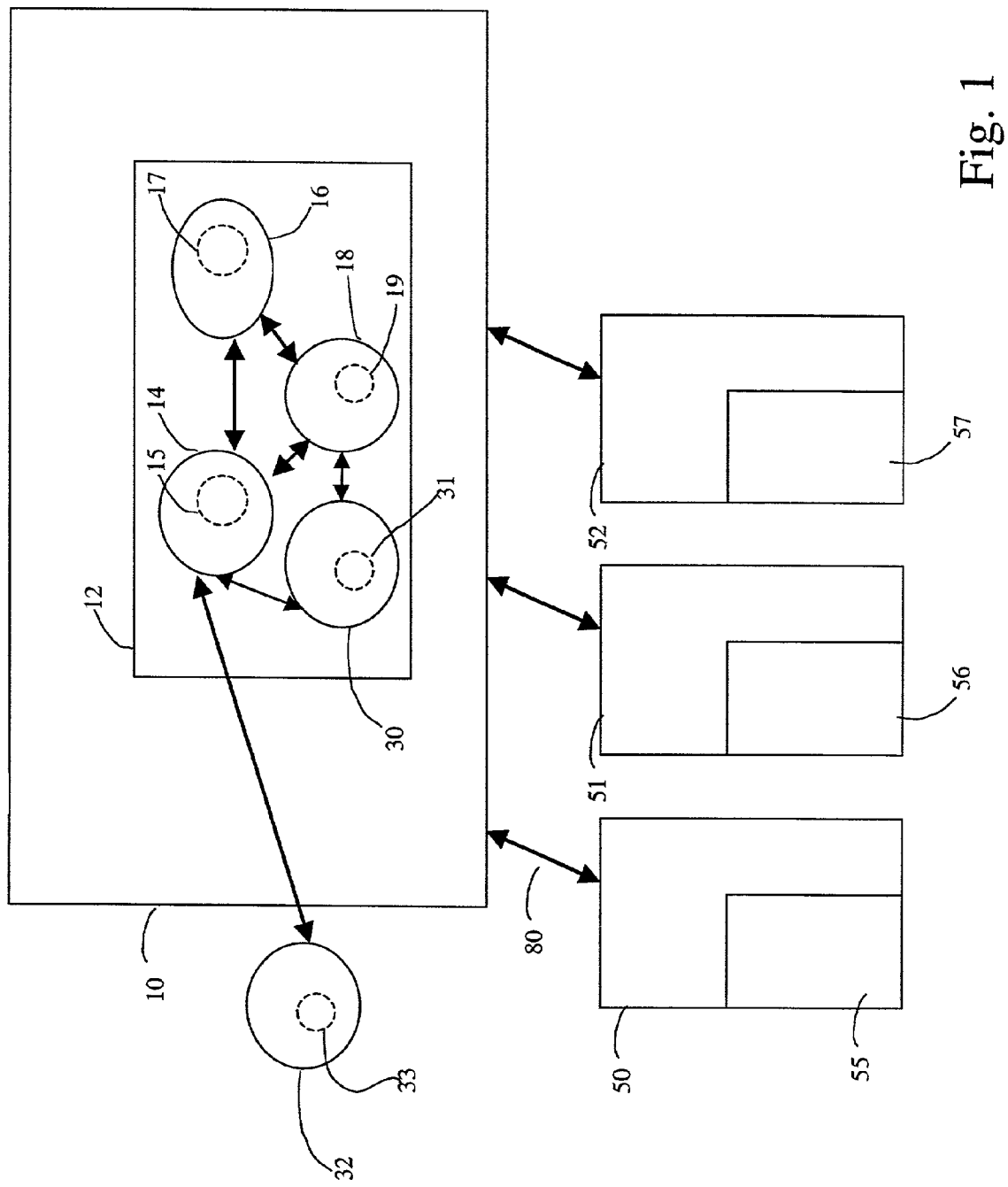
FIG. 1 is a diagram of an embodiment of a system of the invention.

The term "test compound" refers in general to a compound to which a test cell is exposed, about which one desires to collect data. Typical test compounds will be small organic molecules, typically prospective pharmaceutical lead compounds, but can include proteins, peptides, polynucleotides, heterologous genes (in expression systems), plasmids, polynucleotide analogs, peptide analogs, lipids, carbohydrates, viruses, phage, parasites, and the like.

The term "biological activity" as used herein refers to the ability of a test compound to alter the expression of one or more genes.

The term "test cell" refers to a biological system or a model of a biological system capable of reacting to the presence of a test compound, typically a eukaryotic cell or tissue sample, or a prokaryotic organism.

The term "gene expression profile" refers to a representation of the expression level of a plurality of genes in response to a selected expression condition (for example, incubation in the presence of a standard compound or test compound). Gene expression profiles can be expressed in terms of an absolute quantity of mRNA transcribed for each gene, as a ratio of mRNA transcribed in a test cell as compared with a control cell, and the like. As used herein, a "standard" gene expression profile refers to a profile already present in the primary database (for example, a profile obtained by incubation of a test cell with a standard compound, such as a drug of known activity), while a "test" gene expression profile refers to a profile generated under the conditions being investigated. The term "modulated" refers to an alteration in the expression level (induction or repression) to a measurable or detectable degree, as compared to a pre-established standard (for example, the expression level of a selected tissue or cell type at a selected phase under selected conditions).

The term "correlation information" as used herein refers to information related to a set of results. For example, correlation information for a profile result can comprise a list of similar profiles (profiles in which a plurality of the same genes are modulated to a similar degree, or in which related genes are modulated to a similar degree), a list of compounds that produce similar profiles, a list of the genes modulated in said profile, a list of the diseases and/or disorders in which a plurality of the same genes are modulated in a similar fashion, and the like. Correlation information for a compound-based inquiry can comprise a list of compounds having similar physical and chemical properties, compounds having similar shapes, compounds having similar biological activities, compounds that produce similar expression array profiles, and the like. Correlation information for a gene- or protein-based inquiry can comprise a list of genes or proteins having sequence similarity (at either nucleotide or amino acid level), genes or proteins having similar known functions or activities, genes or proteins subject to modulation or control by the same compounds, genes or proteins that belong to the same metabolic or signal pathway, genes or proteins belonging to similar metabolic or signal pathways, and the like. In general, correlation information is presented to assist a user in drawing parallels between diverse sets of data, enabling the user to create new hypotheses regarding gene and/or protein function, compound utility, and the like. Product correlation information assists the user with locating products that enable the user to test such hypotheses, and facilitates their purchase by the user.

A "hypothesis" as used herein refers to a testable idea, inspired in by correlation information, regarding an explanation or model of gene or protein function, biochemical or biological function, drug or compound activity or toxicity, absorption, metabolism, distribution, excretion, and the like. Typical hypotheses herein include, without limitation, the identification of a compound or class of compounds as potential lead compounds or drugs, identification of genes or proteins that are characteristic of a disease state or adverse reaction, identification of genes and/or proteins that interact, and the like.

"Similar", as used herein, refers to a degree of difference between two quantities that is within a preselected threshold. For example, two genes can be considered "similar" if they exhibit sequence identity of more than a given threshold, such as for example 20%. A number of methods and systems for evaluating the degree of similarity of polynucleotide sequences are publicly available, for example BLAST, FASTA, and the like. See also Maslyn et al. and Fujimiya et al., supra, incorporated herein by reference. The similarity of two profiles can be defined in a number of different ways, for example in terms of the number of identical genes affected, the degree to which each gene is affected, and the like. Several different measures of similarity, or methods of scoring similarity, can be made available to the user: for example, one measure of similarity considers each gene that is induced (or repressed) past a threshold level, and increases the score for each gene in which both profiles indicate induction (or repression) of that gene. For example, if $g_x$ is gene "x", and $p_{Ex}$ is the expression level of $g_x$ in an experimental profile, $p_{Sx}$ is the expression level of $g_x$ in a standard profiles, and $p_T$ is a predetermined threshold level, we can define function H for any experimental ("E") and standard ("S") profile pair as $H_{E,S}=1$ when both $p_{Ex}$ and $p_{Sx} \geq p_T$, and $H_{E,S}=0$ when either $p_{Ex}$ or $p_{Sx} < p_T$. Then, a simple similarity score can be defined as $N=\Sigma_x H_x$. This similarity score counts only the genes that are similarly induced in both profiles. A more informative score can be calculated as $N'=\Sigma_x(H_x)*|p_{Ex}-p_{Sx}|*(p_{Ex}*p_{Sx})^{-1/2}$, which also takes into consideration the difference in expression level between the experimental and standard profiles, for each gene induced above the threshold level. Other statistical methods are also applicable.

The term "product information" as used herein refers to information regarding the availability, characteristics, price, and the like, of a product. Product information can consist of a hyperlink to such information. A product "related to data" refers to a product useful for the further exploration of the gene, protein, system, and/or compound to which the data pertains, or to relationships between the gene, protein, system, and/or compound highlighted in the correlation information. Exemplary products include, for example, bioassay kits and reagents, compounds useful as positive and negative controls, kits for purifying proteins or other biological products, antibodies for determining and/or isolating substances, compounds similar to the test compound useful for further study, additional data regarding gene or protein function and/or relationships (for example, sequence data from other species, information regarding metabolic and/or signal pathways to which the gene or protein belong, and the like), DNA microarrays useful for determining expression of the gene and/or related genes, information and analysis regarding features of a compound that are likely to be responsible for the observed activity, and the like.

The term "hyperlink" as used herein refers to feature of a displayed image or text that provides information additional and/or related to the information already currently displayed when activated, for example by clicking on the hyperlink. An HTML HREF is an example of a hyperlink within the scope of this invention. For example, when a user queries the database of the invention and obtains an output such as a list of the genes most induced or repressed by a selected compound, one or more of the genes listed in the output can be hyperlinked to related information. The related information can be, for example, additional information regarding the gene, a list of compounds that affect gene induction in a similar way, a list of genes having a known related function, a list of bioassays for determining activity of the gene product, product information regarding such related information, and the like.

General Method

The system of the invention provides a correlative database that permits one to study relationships between different genes, between genes and a variety of compounds, to investigate structure-function relationships between different compounds, and to facilitate the purchase of products based on such observed relationships. The database contains a plurality of standard gene expression profiles, which comprise the expression level of a plurality of genes under a plurality of specified conditions. The conditions specified can include expression within a particular cell type (for example, fibroblast, lymphocyte, neuron, oocyte, hepatocyte, and the like), expression at a particular point in the cell cycle (e.g., G1), expression in a specified disease state, the presence of environmental factors (for example, temperature, pressure, $CO_2$ partial pressure, osmotic pressure, shear stress, confluency, adherence, and the like), the presence of pathogenic organisms (for example, viruses, bacterial, fungi, and extra- or intracellular parasites), expression in the presence of heterologous genes, expression in the presence of test compounds, and the like, and combinations thereof. The database can contain expression profiles for a plurality of different species, for example, human, mouse, rat, chimpanzee, yeast such as *Saccharomyces cerevisiae*, bacteria such as *E. coli*, and the like. The database preferably comprises expression profiles for at least 10 different genes from a particular organism, more preferably in excess of 500 genes, and can include a substantial fraction of the genes expressed by an organism, such as, for example, about 50%, about 75%, about 90%, or essentially 100%. The standard expression profiles are preferably annotated, for example, with information regarding the conditions under which the profile was obtained. Preferably, the database also contains annotations for one or more genes, more preferably for each gene represented in the database. The annotations can include any available information about the gene, such as, for example, the gene's names and synonyms, the gene's nucleotide sequence the amino acid sequence encoded, any known biological activity or function, any genes of similar sequence, any metabolic or protein interaction pathways to which it is known to belong, a listing of assays capable of determining the activity of its protein product, and the like.

The database contains interpretive gene expression profiles and bioassay profiles for a plurality of different compounds that comprise a representation of a compound's mode of action and/or toxicity ("drug signatures"), and can include experimental compounds and/or "standard" compounds. Drug signatures provide a unique picture of a compound's comprehensive activity in vivo, including both its effect on gene transcription and its interaction with proteins. Standard compounds are preferably well-characterized, and preferably exhibit a known biological effect on host cells and/or organisms. Standard compounds can advantageously be selected from the class of available drug compounds, natural toxins and venoms, known poisons, vitamins and nutrients, metabolic byproducts, and the like. The standard compounds can be selected to provide, as a set, a wide range of different gene expression profiles. The records for the standard compounds are preferably annotated with information available regarding the compounds, such as, for example, the compound name, structure and chemical formula, molecular weight, aqueous solubility, pH, lipophilicity, known biological activity, source, proteins and/or genes it is known to interact with, assays for detecting and/or confirming activity of the compound or related compounds, and the like. Alternatively, one can employ a database constructed from random compounds, combinatorial libraries, and the like.

The database further contains bioassay data derived from experiments in which one or more compounds represented in the database are examined for activity against one or more proteins represented in the database. Bioassay data can be obtained from open literature and directly by experiment.

Further, the database preferably contains product data related to the compounds, genes, proteins, expression profiles, and/or bioassay data otherwise present in the database. The product data can be information regarding physical products, such as bioassay kits and reagents, compounds useful as positive and negative controls, compounds similar to the test compound useful for further study, DNA microarrays and the like, or can comprise information-based products, such as additional data regarding gene or protein function and/or relationships (for example, sequence data from other species, information regarding metabolic and/or signal pathways to which the gene or protein belong, and the like), algorithmic analysis of the compounds to determine critical features and likely cross-reactivity, and the like. The product information can take the form of data or information physically present in the database, hyperlinks to external information sources (such as a vendor's catalog, for example, supplied via the Internet or CD-ROM), and the like.

The database thus preferably contains five main types of data: gene information, compound information, bioassay information, product information, and profile information. Gene information comprises information specific to each included gene, and can include, for example, the identity and sequence of the gene, one or more unique identifiers linked to public and/or commercial databases, its location on a standard array plate, a list of genes having similar sequences, any known disease associations, any known compounds that modulate the encoded protein activity, conditions that modulate expression of the gene or modulate the protein activity, and the like. Product information comprises information specific to the available products, and varies depending on the exact nature of the product, and can include information such as price, manufacturer, contents, warranty information, availability, delivery time, distributor, and the like. Bioassay information comprises information specific to particular compounds (where available), and can include, for example, results from high-throughput screening assays, cellular assays, animal and/or human studies, biochemical assays (including binding assays and enzymatic assays) and the like. Compound information comprises information specific to each included compound, such as, for example, the chemical name(s) and structure of the compound, its molecular weight, solubility and other physical properties, proteins that it is known to interact with, the profiles in which it appears, the genes that are affected by its presence, and available assays for its activity. Profile information includes, for example, the conditions under which it was generated (including, for example, the cell type(s) used, the species used, temperature and culture conditions, compounds present, time elapsed, and the like), the genes modulated with reference to a standard, a list of similar profiles, and the like. The information is obtained by assimilation of and/or reference to currently-available databases, and by collecting experimental data. It should be noted that the gene database, although large, contains a finite number of records, limited by the number of genes in the organisms under study. The compound database is potentially unlimited, as new compounds are made and tested constantly. The profile database, however, is still larger, as it represents information regarding the interaction of a very large number of genes with a potentially infinite number of different compounds, under a variety of conditions.

Experimental data is preferably collected using a high-throughput assay format, capable of examining, for example, the effects of a plurality of compounds (preferably a large number of standard compounds, for example 10,000) when administered individually or as a mixture to a plurality of different cell types. Assay data collected using a uniform format are more readily comparable, and provide a more accurate indication of the differences between, for example, the activity of similar compounds, or the differences in sensitivity of similar genes.

The system provides several different ways to access the information contained within the database. An operator can enter a test gene expression profile into the system, cause the system to compare the test profile with stored standard gene expression profiles in the database, and obtain an output comprising one or more standard expression profiles that are similar to the test profile. The standard expression profiles are preferably accompanied by annotations, for example providing information to the operator as to the similarity of the test profile to standard profiles obtained from disease states and/or standard compounds. The test gene expression profile preferably includes an indication of the conditions under which the profile is obtained, for example a representation of a test compound used, and/or the culture conditions.

The output preferably further comprises a list of the genes that are modulated (up-regulated or down-regulated) in the test gene expression profile, as compared with a pre-established expression value, a pre-selected standard expression profile, a second test gene expression profile, or another pre-set threshold value.

The output is preferably hyperlinked, so that the operator can easily switch from, for example, a listing of the similar standard expression profiles to a listing of the modulated genes in a selected standard expression profile, or from a gene listed in the test profile to a list of the standard expression profiles in which the gene is similarly modulated, or to a list of the standard compounds (and/or conditions) which appear to modulate the selected gene. The output can comprise correlation information that highlights features in common between different genes, targets, profiles, compounds, assays, and the like, to assist the user in drawing useful correlations. For example, the output can contain a list of genes that were modulated in the user's experiment with a selected compound: if a plurality of the genes are indicated as associated with liver toxicity, the system can prompt the user that the compound is associated with a toxic drug signature, and prompt the user to continue with the next compound. Conversely, the output could indicate previously unnoticed associations between different pathways, leading the user to explore a hitherto unknown connection. The output preferably includes hyperlinks to product information, encouraging the user to purchase or order one or more products from a selected vendor, where the product(s) relate specifically to the focus of the database inquiry and the correlation information that results, and is presented back to the user to facilitate hypothesis generation. For example, the output can provide links to products useful for confirming the apparent activity of a compound, for measuring biological activity directly, for assaying the compound for possible side effects, and the like, prompting the user to select products useful in the next stage of experimentation.

The system is preferably provided with an algorithm for assessing similarity of compounds. Suitable methods for comparing compounds and determining their morphological similarity include "3D-MI", as set forth in copending application U.S. Ser. No. 09/475,413, now U.S. Pat. No. 6,470,305, incorporated herein by reference in full, Tanimoto similarity (Daylight Software), and the like. Preferably, the system can be queried for any compounds that are similar to the test compound in structure and/or morphology. The output from this query preferably includes the corresponding standard expression profiles (or hyperlinks to the corresponding standard expression profiles), and preferably further includes a listing, description, or hyperlink to an assay capable of determining the biological activity of the standard and/or test compound.

Thus, for example, if the user inputs an experimental expression profile resulting from incubation of test cells with a particular experimental compound, the user can obtain an output comprising an estimate of the quality of the data, an identification of the genes affected by the compound, a listing of similar profiles and the conditions under which they were obtained (for example, the compounds used), and a list of compounds having a structural similarity. The output can be provided in a hyperlinked format that permits the user to then investigate and explore the data. For example, the user can examine which genes are modulated, and determine whether or not the genes have yet been characterized as to function or activity, and under what conditions each gene is modulated in a similar fashion. Alternatively, the user can compare the profile obtained with the profile of a desired outcome, for example comparing the profile obtained by incubation of diseased or infected tissue with a test compound against a profile obtained from healthy (unperturbed) tissue. Alternatively, the user can compare the profile with the profiles obtained using standard compounds, for example using a drug of known activity, mechanism of action, and specificity, thus determining whether the test compound operates by a different mechanism, or if by the same mechanism whether it is more or less active than the standard. Additionally, the user can compare the structure of the test compound with the structures of other compounds with similar profiles (to determine which structural features of the compounds are common, and thus likely to be important for activity), or can compare the compound's profile with the profiles obtained from structurally similar compounds in general.

The system can be configured as a single, integrated whole, or can be distributed over a variety of locations. For example, the system can be provided as a central database/server with remotely-located access units. The remote access units can be provided with sufficient system capability to accept and interpret test gene expression profiles, and to compare the test profiles with standard gene expression profiles. Remote units can further be provided with a copy of some or all of the database information. Optionally, the remote system can be used to upload test gene expression profiles to the central system to update the central database, or a "private" database supplementary to the main database can be stored in or near the remote unit.

Further, the system can be divided into "vendor" and "client" portions, separating segments of the system into any economically useful subsets, in which interaction between a vendor unit and a client unit is monitored and/or governed by the client's state. For example, the system can be configured to treat a primary database as a vendor unit, and remote access units as client units. The vendor database can be configured to respond to a plurality of different permission levels, wherein lower permission levels are granted access to only a restricted subset of the available data, with successively higher levels obtaining access to greater amounts of data. For example, the lowest permission level can provide access only to publicly-available gene sequences and public annotations, without correlations to compounds or profiles. The client system in such cases can be equipped to provide statistical analysis of the profile generated by the user, the ability to identify genes within the profile, and the ability to compare gene sequences for similarity. In this case, the interaction between client unit and vendor unit can be limited to access to the publicly-available gene sequences, which can be provided electronically, or exchanged via a storage medium (for example, using CD-ROM, DVD, or the like). The bulk of the vendor database (for this permission level) can be pre-installed at the client location, avoiding the need to download large amounts of data (for example, limiting downloads only to updates). This level can be essentially unrestricted, i.e., allowing public access without need for a pre-existing vendor-client relationship.

An intermediate permission level can provide access to a larger subset of data, for example including links to some or all of the available profile and compound data in addition to the information provided to the lower permission level. In this case, the interaction between client and vendor systems occurs contemporaneously or after a client account is established, determining the level of access to be granted the client. If conducted electronically, the interaction is preferably accomplished through means of a secure transaction, to ensure that neither the vendor data nor the client queries are rendered non-confidential. Such transactions can be conducted, for example, by adapting the systems and methods disclosed in U.S. Pat. No. 5,724,424, incorporated herein by reference in full. The data in this case can be limited to compounds that are publicly known (for example, commercially available, or disclosed in patents or the like) and profile data related to those compounds. Alternatively, the system can be arranged so that the client obtains access only to a specific field, for example, profiles related to diabetic conditions, autoimmune conditions, cancer, and the like. For cases of intermediate permission, the vendor system can filter output before it is transmitted to the client system, to insure that only the permitted degree of information is distributed. The vendor system can also filter input, to insure that vendor system resources are not consumed in preparing answers that cannot be delivered to the client system.

At the penultimate permission level, the client is granted access to all data in the database except for data that is proprietary, restricted, or exclusively granted to another client. The ultimate permission level may be available only to the vendor itself, or can be made available to one or more clients if no exclusivity is granted to clients.

Additionally, the system can include provisions for accepting new data from a remote client, for example, to enable a user to store his or her own data on the vendor server. Access to such client data can be restricted to only the same client, or can be made available to all clients or a subset thereof (for example, in exchange for a credit or other privilege).

FIG. 1 illustrates a system of the invention, comprising vendor server 10 containing vendor database 12. Vendor database 12 in turn contains a genomic database 14, a compound database 16, and a profile database 18, which in turn contain optional private (user) databases 15, 17, and 19. Alternatively, the private databases can be physically located outside the vendor databases, for example, elsewhere within the vendor system or maintained in parallel within the user's site. The vendor databases can further comprise a product database 30 maintained within the vendor system, and/or an external product database 32 linked to the vendor system. The product databases can contain information regarding products available from the vendor, a third-party vendor, or both. One or both of the product databases can further comprise user-specific data (31, 33) such as, for example, user account information (account number, format preferences, shipping addresses, prior order history, authorization level, and the like), the user's notes or annotations regarding particular products, and the like. The product databases are preferably provided with hyperlinks that facilitate user purchases of the products displayed. The vendor system is connected to a plurality of user systems 50, 51, 52, which in turn contain individual user databases 55, 56, 57. The user systems can communicate with the vendor system by any convenient medium, including, without limitation, direct connection, distributed network (LAN or WAN), internet connection, virtual private network (VPN), direct dial-in, and the like. The hardware employed for use in the method of the invention can comprise general-purpose computers, for example currently-available personal computers and workstations, or special-purpose terminals designed for this application.

Figure 2:
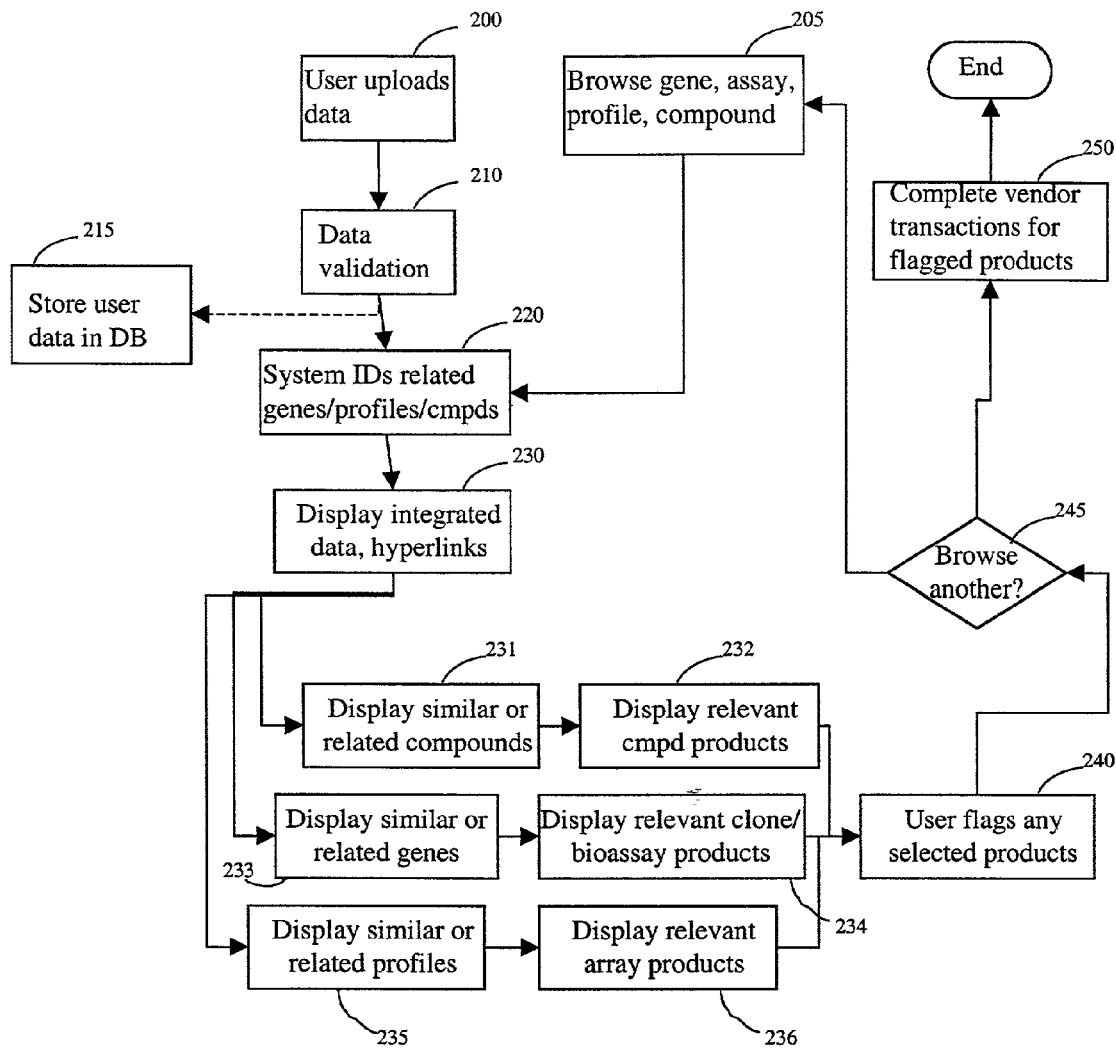
FIG. 2 is a flow diagram illustrating an embodiment of a method of the invention.

FIG. 2 illustrates a simple flow diagram for an embodiment of the invention. The user may begin by uploading data into the system 200 (or otherwise acquiring profile data), or alternatively may simply begin by browsing 205 for a gene, compound, or profile of interest already present in the system. If new data is added, the data can optionally be evaluated and validated 210. Optionally, the new data can be uploaded to the primary database, as either a public or private addition, or can be stored in the user portion of the system 215. After data validation (if any), the data is examined by the system, and the genes and profile identified 220. This result is displayed 230, along with hyperlinks to related product information. Preferably, the results are displayed in a manner that highlights correlations between similar expression profiles, the profiles of similar compounds, the profiles of related genes, and the like. The user can then select more information regarding one or more related compounds 231, genes 233, profiles 235, and the like, at which point the system can display relevant compound products 232, relevant clones and/or bioassay products 234, or relevant array products 236. The output display preferably facilitates selection of relevant products by the user, flagging selected products 240 (for example, adding them to a "shopping cart" system). The user can then select 245 a path of inquiry, and search for compounds of similar structure, morphology, or activity (in terms of profile), for selected genes or genes of similar sequence or known function, or for similar profiles 205. These results are displayed 230, and the user invited to continue browsing until finished. Alternatively, the user can pre-select various forms of output, for example, selecting to have the initial data display include a listing of similar compounds linked to displays of their profiles, or a listing of the experimental profile along with a list of similar profiles ranked by degree of similarity. Alternatively, the user can upload a chemical structure (whether real or hypothetical), and obtain a display of a predicted profile extrapolated from the profiles of morphologically similar compounds.

These methods can be conducted on a single computer, or can be distributed over a plurality of computers. For example, steps 200, 205 and 230 can occur on a remote computer (at the user site), while other steps occur on a local computer or computers, or at another remote site distinct from the user's site (the vendor server).

Data concerning experimental pharmaceutical compounds and their biological activity are extremely sensitive, valuable and confidential. In embodiments that include computers or other hardware at a plurality of locations, it is presently preferred to include some provision for security, for example by regulating access or by means of encrypted commands and results. Suitable methods are known in the art, including, for example, public key encryption and SSL (secure socket layer) connections. Alternatively, rather than reporting gene expression data in terms of absolute expression, one can report the data in terms of differences from a given standard. Thus, if gene "A" has an arbitrary standard expression value of 56 (in arbitrary units), and in an experimental profile gene "A" is expressed at a level of 97, the data for gene "A" can be reported as expression of 41 rather than 97. A different standard level can be established for each gene employed, essentially forming an encoding profile. A plurality of different encoding profiles can be established and enumerated for each user and shared by secure means, with the user and vendor simply indicating which profile (by number) is used for each transmission. Further, one can express the data in terms of other arithmetic functions and combinations of functions of an encoding profile, as long as the original data can be unambiguously retrieved by the authorized party. For example, the encoding transform for a particular encoding profile can specify that data for the first gene is expressed as the difference between the experimental and profile values, while data for the next gene is expressed as a percentage of the profile value, while data for the third gene is expressed as the difference between the third experimental value and the second experimental value, and the like. If additional security is desired, one can establish encoding profiles and transforms that change depending on other parameters, for example by date, by user number, by time of file modification, by number of data sets, and the like, and combinations thereof. Alternatively, one can specify a large number of available encoding profiles, and specify in advance a random sequence of profiles to employ, avoiding the identification of any profile during transmission of data.

What is claimed is:

1. A method for analyzing chemical genomic data, comprising:
    a) providing a database in a computer readable medium comprising at least the following four data types: (i) profile information comprising a representation of the expression level of a plurality of genes in a cell exposed to a standard compound; (ii) bioassay information; (iii) gene information; and (iv) compound information for each of the plurality of standard compounds; wherein the information in any of the data types may be accessed through a query in any other data type;
    b) selecting at least a first database record from any of the data types; and
    c) determining and displaying correlation information related to the selected first database record;
    d) selecting at least a second database record from the correlation information, wherein the second database record is from a different data type than the first database record;
    e) determining and displaying product information associated with the second database record;
    f) selecting at least one product associated with the product information.

2. The method of claim 1, wherein said correlation information is selected from the group consisting of: identification of one or more similar profiles, identification of one or more standard compounds that produce similar profiles, identification of one or more genes modulated in a profile or a similar profile, identification of a disease or disorder in which a plurality of the same genes are modulated in a similar fashion, identification of one or more compounds having similar physical and chemical properties as the standard compound used to generate a profile, identification of one or more compounds having similar shapes, identification of one or more compounds having similar biological activities, identification of one or more genes or proteins having sequence similarity, identification of one or more genes or proteins having a similar function or activity, identification of one or more genes or proteins subject to modulation or control by the same standard compound(s), and identification of one or more genes or proteins that belong to the same or a similar metabolic or signal pathway.

3. The method of claim 1, wherein said product is selected from the group consisting of: a bioassay reagent useful for measuring activity of an identified enzyme, a compound useful as a positive control, information regarding a compound useful as a negative control, a kit for purifying an identified protein, antibodies for determining and/or isolating substances, a test compound useful for further study, additional data regarding a gene's or protein's function and/or relationships, sequence data from other species, information regarding metabolic and/or signal pathways to which a gene or protein belong, a DNA microarray useful for determining expression of a gene and/or related genes, and information and analysis regarding features of a compound that are likely to be responsible for the observed activity.

4. The method of claim 1, wherein displaying product information further comprises providing a hyperlink that facilitates direct purchase of a product identified by the product information.

5. The method of claim 1, wherein said database further comprises drug signatures for a plurality of standard compounds, wherein each said drug signature comprises a representation of the physical and chemical characteristics of each compound, data regarding the effect of each compound on the transcription of a plurality of genes, data regarding the effect of each compound on a plurality of proteins and bioassay data regarding the in vivo effect of each compound.

6. The method of claim 1, wherein the first database record selected is a standard gene expression profile selected on the basis of its similarity to an experimental expression profile provided by the user.

7. A method for analyzing chemical genomic data, comprising:
    a) providing a database in a computer readable medium comprising drug signatures for each of a plurality of compounds, wherein said drug signatures comprise at least the following data types: (i) a representation of the physical and chemical characteristics of the compound; (ii) data regarding the effect of the compound on the transcription of a plurality of genes; (iii) data regarding the effect of the compound on a plurality of proteins; and (iv) bioassay data regarding the in vivo effect of the compound; wherein the information in any of the data types may be accessed through a query in any other data type;
    b) selecting at least one drug signature;
    c) determining and displaying correlation information related to at least one data type of said selected drug signature;
    d) selecting at least a second drug signature based on the correlation information;
    e) determining and displaying product information associated with the second drug signature;
    f) selecting at least one product associated with the product information.

8. The method of claim 7, wherein said product is selected from the group consisting of: a bioassay reagent useful for measuring activity of an identified enzyme, a compound useful as a positive control, a compound useful as a negative control, a kit for purifying an identified protein, information regarding antibodies for determining and/or isolating substances, a test compound useful for further study, additional data regarding a gene's or protein's function and/or relationships, sequence data from other species, information regarding metabolic and/or signal pathways to which a gene or protein belong, a DNA microarray useful for determining expression of a gene and/or related genes, and information and analysis regarding features of a compound that are likely to be responsible for the observed activity.

9. The method of claim 7, wherein displaying product information further comprises providing a hyperlink that facilitates direct purchase of a product identified by the product information.

10. A system for analyzing chemical genomic data, comprising:
- a computer readable medium having encoded thereon a database comprising at least the following four data types: (i) profile information comprising a representation of the expression level of a plurality of genes in a cell exposed to a standard compound; (ii) bioassay information; (iii) gene information; and (iv) compound information for each of the plurality of standard compounds; wherein the information in any of the data types may be accessed through a query in any other data type;
- a computer readable medium having encoded thereon a set of instructions for:
  - (i) user data input;
  - (ii) user selection of at least a first database record from any of the data types;
  - (iii) display and user selection of correlation information related to said selected first database record;
  - (iv) user selection of at least a second database record related to said first database record;
  - (v) display of product information associated with said second database record; and
  - (vi) user selection of at least one product associated with the product information.

11. The system of claim 10, wherein said database further comprises drug signatures for a plurality of compounds, wherein each said drug signature comprises a representation of the physical and chemical characteristics of each compound, data regarding the effect of each compound on the transcription of a plurality of genes, data regarding the effect of each compound on a plurality of proteins, and bioassay data regarding the in vivo effect of each compound.

12. A system for analyzing chemical genomic data, comprising:
- a computer readable medium having encoded thereon a database comprising drug signatures for each of a plurality of compounds, wherein each said drug signature comprises at least the following data types: (i) a representation of the physical and chemical characteristics of the compound; (ii) data regarding the effect of the compound on the transcription of a plurality of genes; (iii) data regarding the effect of the compound on a plurality of proteins; and (iv) bioassay data regarding the in vivo effect of the compound; wherein the information in any of the data types may be accessed through a query in any other data type;
- a computer readable medium having encoded thereon a set of instructions for:
  - (i) user data input;
  - (ii) user selection of at least one drug signature;
  - (iii) display and user selection of correlation information related to at least one data type of said selected drug signature;
  - (iv) user selection of at least a second drug signature based on the correlation information;
  - (V) display of product information associated with the second drug signature; and
  - (vi) user selection of at least one product associated with the product information.

13. The method of claim 3, wherein the selected product is a DNA microarray.

14. The method of claim 8, wherein the selected product is a DNA microarray.

* * * * *